United States Patent
Podella

(10) Patent No.: US 12,146,181 B2
(45) Date of Patent: *Nov. 19, 2024

(54) COMPOSITIONS AND METHODS FOR ENHANCING EFFICIENCIES OF MICROBIAL-DERIVED BIOSURFACTANTS

(71) Applicant: Advanced BioCatalytics Corporation, Irvine, CA (US)

(72) Inventor: Carl W. Podella, Irvine, CA (US)

(73) Assignee: Advanced BioCatalytics Corporation, Irvine, CA (US)

( * ) Notice: Subject to any disclaimer, the term of this patent is extended or adjusted under 35 U.S.C. 154(b) by 237 days.

This patent is subject to a terminal disclaimer.

(21) Appl. No.: 17/542,285

(22) Filed: Dec. 3, 2021

(65) Prior Publication Data

US 2022/0090150 A1  Mar. 24, 2022

Related U.S. Application Data

(63) Continuation of application No. 16/947,689, filed on Aug. 12, 2020, now Pat. No. 11,220,699.

(51) Int. Cl.
*C12N 9/20* (2006.01)
*C12P 1/02* (2006.01)
*C12P 7/6436* (2022.01)

(52) U.S. Cl.
CPC .............. *C12P 7/6436* (2013.01); *C12P 1/02* (2013.01)

(58) Field of Classification Search
CPC ................ C12N 9/20; C12P 7/64; C12P 1/02
See application file for complete search history.

(56) References Cited

U.S. PATENT DOCUMENTS

| | | | |
|---|---|---|---|
| 2,320,479 A | 6/1943 | Sperti | |
| 3,404,068 A | 10/1968 | Battistoni | |
| 3,635,797 A | 1/1972 | Battistoni et al. | |
| 5,238,925 A | 8/1993 | Bentley | |
| 5,356,874 A | 10/1994 | Bentley | |
| 5,514,591 A | 5/1996 | Levin | |
| 5,714,169 A | 2/1998 | Levin | |
| 5,820,758 A | 10/1998 | Dale et al. | |
| 5,849,566 A | 12/1998 | Dale et al. | |
| 5,885,950 A | 3/1999 | Dale et al. | |
| 5,897,928 A | 4/1999 | Sanders et al. | |
| 6,033,875 A | 3/2000 | Bussineau et al. | |
| 6,046,152 A | 4/2000 | Vinson et al. | |
| 6,280,481 B1 | 8/2001 | Storey-Laubach et al. | |
| 6,284,230 B1 | 9/2001 | Sako et al. | |
| 6,682,924 B1 | 1/2004 | Sierkstra et al. | |
| 7,348,168 B2 | 3/2008 | Wu et al. | |
| 7,645,730 B2 | 1/2010 | Baldridge et al. | |
| 7,659,237 B2 | 2/2010 | Baldridge et al. | |
| 8,188,028 B2 | 5/2012 | Baldridge et al. | |
| 11,220,699 B1* | 1/2022 | Podella | C12P 7/6436 |
| 2002/0115582 A1 | 8/2002 | Perry et al. | |
| 2005/0074417 A1 | 4/2005 | Chen | |
| 2005/0095218 A1 | 5/2005 | Degenhardt et al. | |
| 2005/0137116 A1 | 6/2005 | Overdevest | |
| 2006/0270583 A1 | 11/2006 | Baldridge et al. | |
| 2008/0167445 A1 | 7/2008 | Podella et al. | |
| 2008/0171091 A1 | 7/2008 | Wood et al. | |
| 2010/0113324 A1 | 5/2010 | Baldridge et al. | |
| 2012/0238485 A1 | 9/2012 | Baldridge et al. | |

FOREIGN PATENT DOCUMENTS

WO        WO9707202 A1        2/1997

OTHER PUBLICATIONS

"Is Harvesting Palm Oil Destroying the Rainforests?," retrieved on 2020 at <<https://www.scientificamerican.com/article/harvesting-palm oil-and-rainforests>>, 5 pages.
Bentley, et al., "Peptides From Live Yeast Cell Derivative Stimulate Wound," Healing. Arch. Surg., vol. 5, 1990, pp. 641-646.
Chen, et al., "Sophorolipid produced from the new yeast strain *Wickerhamiella domercqiae* induces apoptosis in H7402 human liver cancer cells," Appl Microbiol Biotechnol., vol. 72, No. 1, 2006, pp. 52-59.
Dolman, et al., "Integrated sophorolipid production and gravity separation," Process Biochemistry, 2016, 35 pages.
Fleurackers, Steve J.J., "On the use of waste frying oil in the synthesis of sophorolipids," Eur. J. Lipid. Sci. Technol., vol. 108, No. 1, 2006, pp. 5-12.
Kurtzman, et al., "Production of sophorolipid biosurfactanls by multiple strains of the Starmerella (Candida) bombicola yeast clade," FEMS Microbiol. Lett., vol. 311, No. 2, 2010, pp. 140-146.
Low & Chase, "Reducing Production of Excess Biomass During Wastewater Treatment," Wal. Res., vol. 5, 1998, pp. 1119-1132.
Low & Chase, et al., "The Use of Chemical Uncouplers for Reducing Biomass Production Durin Biodegradalion," Wal. Sci. Tech., vol. 37, No. 4-5, 1998, pp. 399-402.
Pandolfe, William D., "Cell Disruption by Homogenization," APV-Gaulin Tachnical Bulletin, 1992, 11 pages.
Parekh & Pandit, "Optimization of fermentative production of sophorolipid biosurfactant by starmerella bombicola NRRL Y-17069 using response surface methodology," Internl. J. Pharm. Biol. Sci., vol. 1, No. 3, 2011, pp. 103-116.
Reed & Nagodawithana, "Chapter 6: Bakers Yeast Production," In Yeast Technology, Springer, Dordrecht (CR) Van Nostrand, Reinhold 1991, pp. 261-313.
Russell & Cook, "Energetics of Bacterial Growth: Balance of Anabolic and Calabolic Reactions, " Microbiol. Rev., vol. 59, No. 1, 1995, pp. 48-62.
Schlemm, et al., "Medicinal Yeast Extracts," Cell Stress and Chaperones, vol. 4, No. 3, 1999, pp. 171-176.
Shah, et al., "Sophorolipids, microbial glycolipids with anti-human immunodeficiency virus and sperm-immobilizing activities," Antimicrob. Agents Chemother., vol. 49, No. 10, 2005, pp. 4093-4100.

(Continued)

*Primary Examiner* — Tekchand Saidha
(74) *Attorney, Agent, or Firm* — Lee & Hayes, P.C.

(57) ABSTRACT

Disclosed herein are compositions comprising a sophorolipid surfactant and a bio-synergist and the methods of using the same.

10 Claims, 6 Drawing Sheets

(56) References Cited

OTHER PUBLICATIONS

Van Bogaert, ir. Inge, "Microbial synthesis of sophorolipids by the yeast *Candida bombicola*," PhD-thesis, Faculty of Bioscience Engineering, Ghent University, Ghent, Belgium, 2008, 239 pages.
Van Bogaert, et al., "Microbial synthesis of sophorolipids," Process Biochemistry, vol. 46, No. 4, 2011, pp. 821-833.
Wadekar, et al., "Sophorolipid Production by Starmerella bombicola (ATCC 22214) from Virgin and Waste Frying Oils, and the Effects of Activated Earth Treatment of the Waste Oils," JAOCS, vol. 89, No. 6, 2012, pp. 1029-1039.

* cited by examiner

COMPOSITIONS AND METHODS FOR ENHANCING EFFICIENCIES OF MICROBIAL-DERIVED BIOSURFACTANTS

RELATED APPLICATION

This is a continuation of co-pending U.S. patent application Ser. No. 16/947,689, filed Aug. 12, 2020, the entire disclosure of which is incorporated by reference herein.

FIELD OF THE INVENTION

The present invention is in the field of compositions comprising surfactants and stressed yeast metabolite broth.

BACKGROUND OF THE DISCLOSURE

Petroleum-based surfactants are produced to yield a wide range of performance attributes, but have many inherent disadvantages, with the greatest being their contribution to the depletion of non-renewable resources. Many can cause environmental problems due to bio-degradability issues or simply incompatibility with nature. Plant-based surfactants, such as palm, coconut or soybean oils, do have the advantage of being based on renewable sources. But some of these sources are also having a negative impact on the environment, as these trees are grown in rainforest areas and their cultivation leads to global rainforest depletions. Further, both plant and petroleum-based surfactants potentially contribute to skin irritation and allergies.

A relatively new family of bio-surfactants, known as sophorolipid surfactants, is beginning to gain popularity. Sophorolipids are glycolipids with a hydrophobic fatty acid tail of about 16 to 18 carbon atoms and a hydrophilic sophorose head, and are produced by various non-pathogenic yeast species such as *Candida apicola, Rhodotorula bogoriensis, Wickerhamiella domercqiae,* and *Starmerella bombicola.*

SUMMARY OF THE INVENTION

Disclosed herein are compositions comprising a sophorolipid surfactant and a bio-synergist and the methods of using the same.

DETAILED DESCRIPTION OF THE EMBODIMENTS

Figure 1:
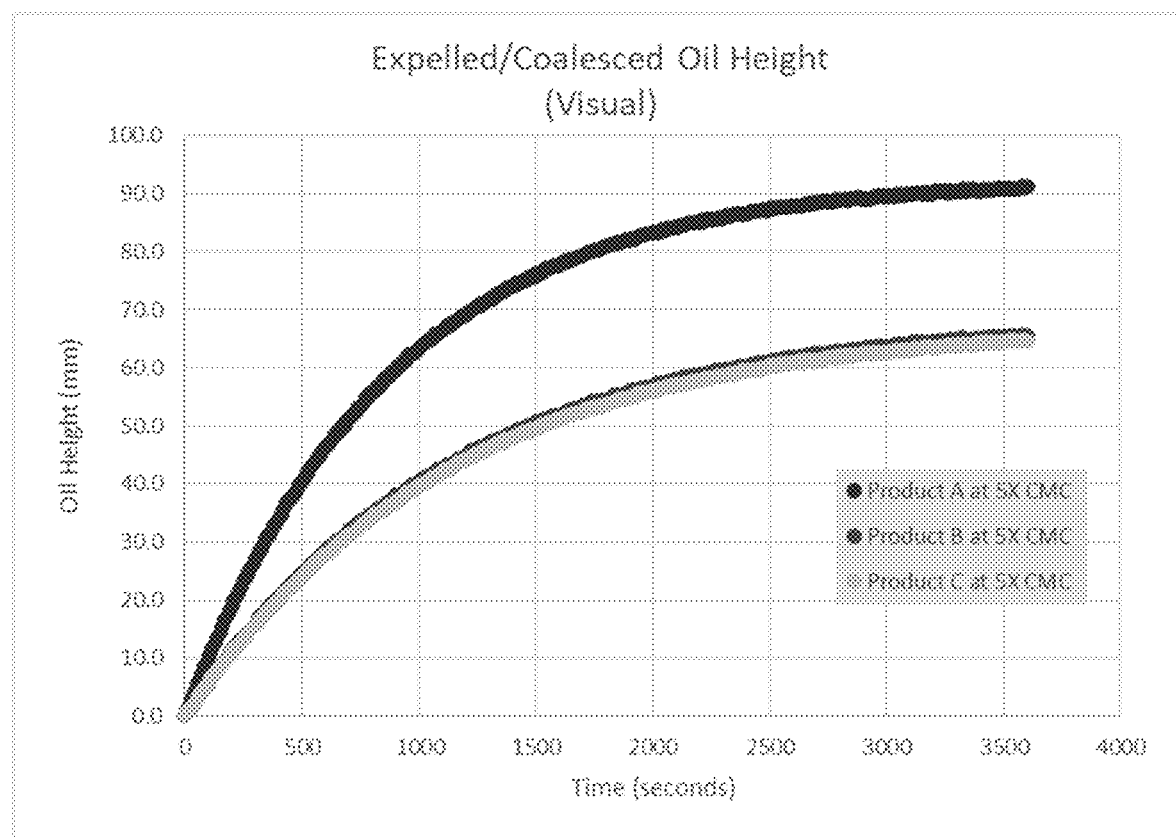
FIG. 1 is a graph showing the height of coalesced oil in a column comparing three different compositions as disclosed herein.

Disclosed herein are bio-surfactant compositions (BSC) that comprise a surfactant bio-synergist (SBS). The compositions comprise a sophorolipid surfactant as the primary surfactant, and a stressed yeast derived metabolite broth (SBS) that has the effect of improving the surface-active properties of the aforementioned bio-surfactants contained in the composition. In some embodiments, the stressed yeast derived metabolite broth is the SBS. The compositions disclosed herein result in a significantly lower critical micelle concentration (CMC), lower concentration of larger micelles, and greater cleaning performance than bio-surfactants alone. The presence of the SBS in the presently disclosed compositions allow for a lower concentration of the sophorolipid surfactant than would otherwise be needed to achieve a desired level of surface-activity and cleaning performance, which in turn reduces the negative environmental impact of the surfactant use.

In some embodiments, the SBS comprises a metabolite broth produced by an aerobic yeast fermentation process that is stressed in the manners described below. The aerobic yeast fermentation process is conducted within a reactor having aeration and agitation mechanisms, such as aeration tubes and/or mechanical agitators. The starting materials (liquid growth medium, yeast, sugars, additives) are added to the fermentation reactor and the fermentation is conducted as a batch process. This method of fermentation is well-known to a person of ordinary skill in the art (POSITA). In an alternative embodiment, the yeast in the production of the sophorolipid surfactants is separated from the spent nutrient source and used.

After fermentation, the yeast is subjected to additional procedures intended to create the SBS. Examples of these additional procedures include heat shock of the fermentation product, physical and/or chemical disruption of the yeast cells to release additional substances, lysing of the yeast cells, or other procedures described herein and/or known to those of skill in the art. Detailed processes for the stress inducing procedures are disclosed in U.S. Pat. No. 7,659, 237, especially at column 3, line 1 to column 4 line 51, which disclosure is incorporated by reference herein.

In some embodiments, the yeast cells are removed by centrifugation or filtration to produce a supernatant containing the SBS. In certain embodiments, the remaining solid yeast cell debris is separated from the water soluble surfactant bio-synergist fluid and may be used for other purposes, for example, livestock feed.

The SBS produced by the presently described processes comprises metabolites having a variety of molecular weights that have been found to be useful for improving surface-active properties of sophorolipid surfactants. Although the composition of the present invention is preferably obtained by the foregoing fermentation process, the component may also be obtained by alternative methods, such as the direct synthesis or isolation of the constituents from other naturally occurring source.

In some embodiments, using the SBS in conjunction with commercially available sophorolipid surfactants in certain ratios, the present inventors found that each case resulted in significantly lower CMC, larger micelle sizes, and greater cleaning performance in comparison with sophorolipid surfactants alone.

This modification of the sophorolipid surfactants' functionality through the use of the compositions disclosed herein has a significant importance in the overall performance of the products developed across a broad scope of applications and the reduction of the amounts of sophorolipid surfactant required to accomplish a specific job. The BSCs disclosed herein allow for the use of a lower amounts of the sophorolipid surfactant, which reduces the product's carbon footprint, or the level of pollution as a result of activities, like washing clothes. Thus, the use of the BSCs disclosed herein reduces the organic load on municipal wastewater treatment plants.

Reducing the cleaning solution residue will reduce the potential for allergic reactions for people with hypersensitivity to chemicals. Window cleaners and all-purpose cleaners' performance can be improved using less surfactants, thereby reducing the levels of streaking and haze after use. And the performance of dishwashing detergents will be extended when washing grease and oil-laden dishes and cooking utensils, just to name a few benefits.

The sophorolipid surfactants used as examples, without limitation, are: *Candida bombicola* sophorolipids (CBS) made as the partially hydrolyzed fermentation product of *Candida bombicola* with glucose; and those described in Dolman et al., "Integrated sophorolipid production and gravity separation," Process Biochemistry, 2017, 54, 162-171.

Micelles are initially formed as a set number of molecules per micelle, regardless of the concentration of the surfactant in the mixture based on head group to tail group spacing relationships of the surfactants, which directly affect the thermodynamics of micelle formation. Even if a micelle is initially formed with a few less molecules as the kinetic product, the final thermodynamically dictated number of molecules per micelle are always obtained. For example, SDS, being anionic, forms micelles with about 80 surfactant molecules per micelle. Non-ionic surfactants, such as Tween surfactants (Polyoxyethylene sorbitan monooleate), on the other hand, form micelles with up to 400 molecules per micelle. The electrostatic interactions of the ionic head of SDS explains in part the lower number of molecules per micelle.

Typically, when head groups repel each other less one obtains a lower CMC and larger number of surfactants per micelle.

The number of oil molecules a micelle can take up is dependent on the micelle size. The larger the micelle, the more oil it traps. Therefore, in cleaning applications, Larger micelles are more desirable.

As the concentration of surfactant increases, that concentration will reach a point where hexagonal and lamella phases will be formed, phases which are extended and essential infinite micelles respectively.

The SBS helps head groups tolerate each other better by reducing their mutual repulsion. The head groups are then closer together, reducing the micelle surface curvature, and increasing the radius. Consequently, the micelle is capable of accommodating more surfactants per micelle, have a larger micelle than would be obtained without the SBS, and be able to trap more oil molecules.

The low CMC thus obtained leads to two results: 1) the solution can be diluted much further from the concentrate and still have micelles, and 2) the micelles created are typically larger, therefore they are able to hold more oil per amount of surfactant used.

Thus, disclosed herein are compositions comprising a sophorolipid surfactant and a surfactant bio-synergist (SBS). In some embodiments, the SBS is a metabolite broth produced by an aerobic yeast fermentation process, followed by a stress step. In certain embodiments, the stress step comprises heat shock of the fermentation product, physical and/or chemical disruption of the yeast cells, or lysing of the yeast cells. In some embodiments, the sophorolipid surfactant is a partially hydrolyzed fermentation product of *Candida bombicola* with glucose, forming C18-unsaturated fatty acids esters with glycerol.

In some embodiments, the composition comprises about 10% sophorolipid surfactant, about 20% sophorolipid surfactant, about 30% sophorolipid surfactant, about 40% sophorolipid surfactant, or about 70% sophorolipid surfactant. In some embodiments, the composition comprises about 30% SBS, about 50% SBS, about 70% SBS, about 80% SBS, or about 90% SBS. In some embodiments, the ratio of the sophorolipid surfactant to the SBS in the composition is selected from the group consisting of about 70:30, about 50:50, about 30:70, about 20:80, and about 10:90.

In some embodiments, the critical micelle concentration of the composition is between about 0.1% to about 0.5% of the composition.

In some embodiments, the composition retains at least about 30% of the oil trapped by the micelles in the composition after one hour, whereas in other embodiments, the composition retains greater than about 20% of the oil trapped by the micelles in the composition after one hour.

By "about" a certain value it is meant that the stated value comprises the range of values within ±25%, ±20%, ±10%, or ±5% of the stated value. Thus, by way of example only, if a distance is given as "about 5 mm," the range of distances between 3.75 mm (5-25%) to 6.25 mm (5+25%) is envisioned.

EXAMPLES

Example 1: Effect of SBS on CMC—First Experiment

A BSC combination of sophorolipid surfactant (CBS) and SBS was tested and resulted in a lower CMC value than the surfactant alone, thus demonstrating the ability to achieve dramatically lower sophorolipid surfactant concentrations while achieving a surface tension equal to or less than the sophorolipid surfactant only. This type of feature is important in the formulation of glass cleaners or similar type applications where the resulting residual surfactant from the glass cleaning activity can leave streaking or a haze, thus detracting from the overall performance of the product.

CBS was evaluated to determine the CMC by determining the Surface Tension (ST) over a range of ever-increasing surfactant concentrations (wt. %) starting at 0.010% and terminating at 2.5%.

CBS alone attained a CMC value of 0.132% and a ST of 38.68 mN/m. The SBS, which contained 2.0% of CBS as a stabilizing agent, was also tested and its CMC was determined to be 1.864% and the ST was 38.57 mN/m. The surfactant and SBS were combined at different ratios to determine the effect of the SBS on the surfactant in reducing the CMC values of those blends. The ratios of surfactant to SBS were about 70:30, about 50:50, about 30:70, about 20:80, and about 10:90. All test results were determined from 40-point CMC plots using a Kruss DSA 100 drop shape analysis at 25° C. The results are shown in Table 1.

TABLE 1

| Sample | CMC | ST |
| --- | --- | --- |
| 100% CBS | 0.132 | 38.57 |
| 70% CBS-30% SBS | 0.169 | 39.07 |
| 50% CBS-50% SBS | 0.142 | 38.80 |

TABLE 1-continued

| Sample | CMC | ST |
|---|---|---|
| 30% CBS-70% SBS | 0.125 | 38.10 |
| 20% CBS-80% SBS | 0.175 | 39.24 |
| 10% CBS-90% SBS | 0.391 | 40.04 |
| 100% SBS | 1.861 | |

Example 2: Effect of SBS on CMC—Second Experiment

These series of experiments demonstrated the ability of the SBS to increase the performance of the surfactant in terms of overall durability, for example, achieving greater cleaning ability of a formulation without increasing the amount of product required to achieve a specific goal. This can be demonstrated in a liquid dishwashing detergent where 10 mL of a sophorolipid-based dishwashing detergent may have the cleaning power to clean X number of plates soiled with a standard artificial food soil. The addition of SBS to the mixture will reduce the needed amount of CBS, which is the costliest ingredient, without negatively affecting the cleaning power of the solution. Thus, in this example, 10 mL of the mixture of CBS and SBS can still clean X number of plates, while using less CBS, as measured by the reduced CMC values.

Addition of SBS to the mixture, along with reducing the cost, reduces the environmental footprint of the cleaning mixture. Reducing the surfactant load reduces the organic loading needing to be processed in wastewater treatment plants while reducing the levels of sludge, $CO_2$ and methane that are byproducts of the wastewater treatment processes. The carbon footprint, the amount of palm oil, or other plant-based oils to produce a similar product, are reduced as well. In general, the mixtures disclosed herein reduce the environmental impact for raw materials, production and eventual disposal of the product in comparison with similar products, while facilitating the formulation of superior performing products without sacrificing the environments.

CBS was evaluated to determine the CMC of the surfactant where the surfactant is maintained at a constant concentration (10% for example), and the SBS was added to create the various ratios of surfactant to synergist. Using the above example of a 10% surfactant concentration, a 50%/50% ratio would result in having a 10% surfactant and 10% synergist combination. These results are compared with those in Example 1 and provided in Table 2.

TABLE 2

| Sample | CMC | ST |
|---|---|---|
| 100% CBS | 0.132 | 38.57 |
| 70% CBS-30% SBS | 0.120 | 39.07 |
| 50% CBS-50% SBS | 0.075 | 38.80 |
| 30% CBS-70% SBS | 0.0378 | 38.10 |
| 20% CBS-80% SBS | 0.036 | 39.24 |
| 10% CBS-90% SBS | 0.0395 | 40.04 |
| 100% SBS | 1.861 | |

As shown, the overall reduction of the CMC value by the addition of the SBS (20% CBS/80% SBS) results in a 3.5-fold increase in cleaning power (132/36=3.5). Alternatively, combinations of Examples 1 and 2 allows the formulator to balance the performance attributes to achieve cost/benefit optimization.

Example 3: Determination of Micelle Oil Holding Capacity

An experimental design was developed in which aqueous surfactant solutions (proposed products at specific concentrations) are prepared, mixed with oils, then their separation was monitored, both visually and through conductivity measurements at specific points along the column of emulsified fluid. The apparatus was attached to a conductivity meter for picosiemen/meter range (low conductivity oil range). A conductivity sensor from a Teclis Foamscan instrument was also used to measure the aqueous continuous emulsion phases.

The conductivity sensors were placed at 220 mm, 130 mm, 80 mm, and 30 mm above the base of the column. The column was 245 mm high and 30 mm in diameter. It was filled to 240 mm with 165 mL of liquid. For all measurements made in this set 82.5 mL of corn oil and 82.5 mL of the diluted BSC were used.

For each experiment, the corn oil and the BSC solution were mixed in a sonication bath for 60 seconds and then quickly poured it into the column.

Conductivities for oils and surfactant solutions are grossly different. Aqueous surfactant solutions have the conductivities in the 100's of microsiemens/meter range, whereas oils are in the nanosiemens/meter to picosiemens/meter range, depending on how polar they are. Therefore, when conductivities across the electrodes are measured, it is relatively easy to relate the measured value to the percentage of water at that position in the emulsion. The amount of oil in the mixture then is the remainder, i.e., 100%−water %=oil %.

Three formulations were evaluated for their oil "holding" ability. They were:

Product "A"=10% Sophorolipid (CBS); 90% DI Water.
Product "B"=3.0% Sophorolipid (CBS); 7.0% SBS; 90% DI Water.
Product "C"=10.0% Sophorolipid (CBS); 23.3% SBS; 66.7% DI Water.

"DI water" refers to deionized water.

Product "A" had a CMC of 1.32 wt %. It was tested diluted to 5×CMC, so 82.5 mL of 6.60 wt % Product "A" in DI Water was combined with 82.5 mL of corn oil for the first test.

Product "B" had a CMC of 1.26 wt %. It was tested diluted to 5×CMC, so 82.5 mL of 6.30 wt % Product "B" in DI Water was combined with 82.5 mL of corn oil for the second test.

Product "C" is in effect a 3.33× version of Product "B", both surfactants and SBS are just multiplied in concentration by 3.33. So the CMC of Product "C" is 1.26/3.33=0.378%. It was tested diluted to 5×CMC, so 82.5 mL of 1.89 wt. % Product "C" in DI Water was combined with 82.5 mL of corn oil for our third test.

Figure 2:
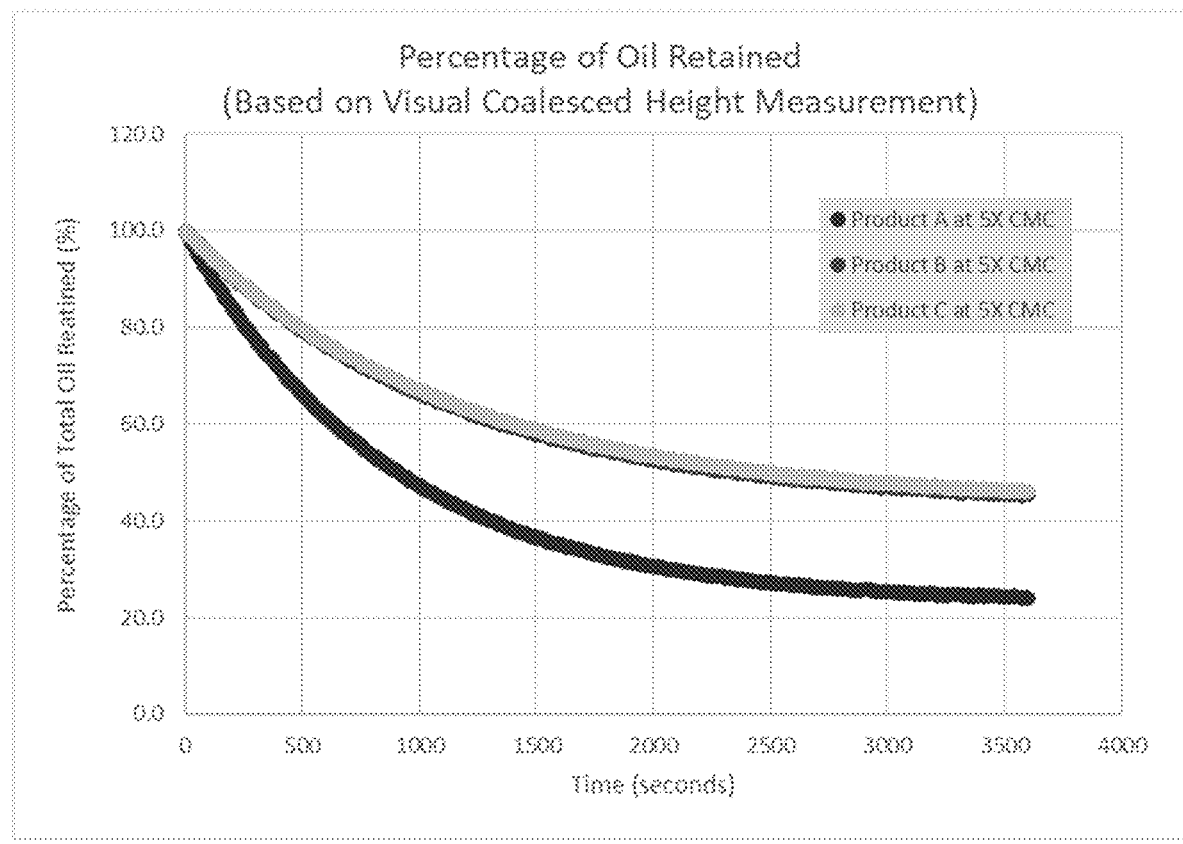
FIG. 2 is a graph showing the percentage of oil retained by micelles in a column comparing three different compositions as disclosed herein.
Figure 3:
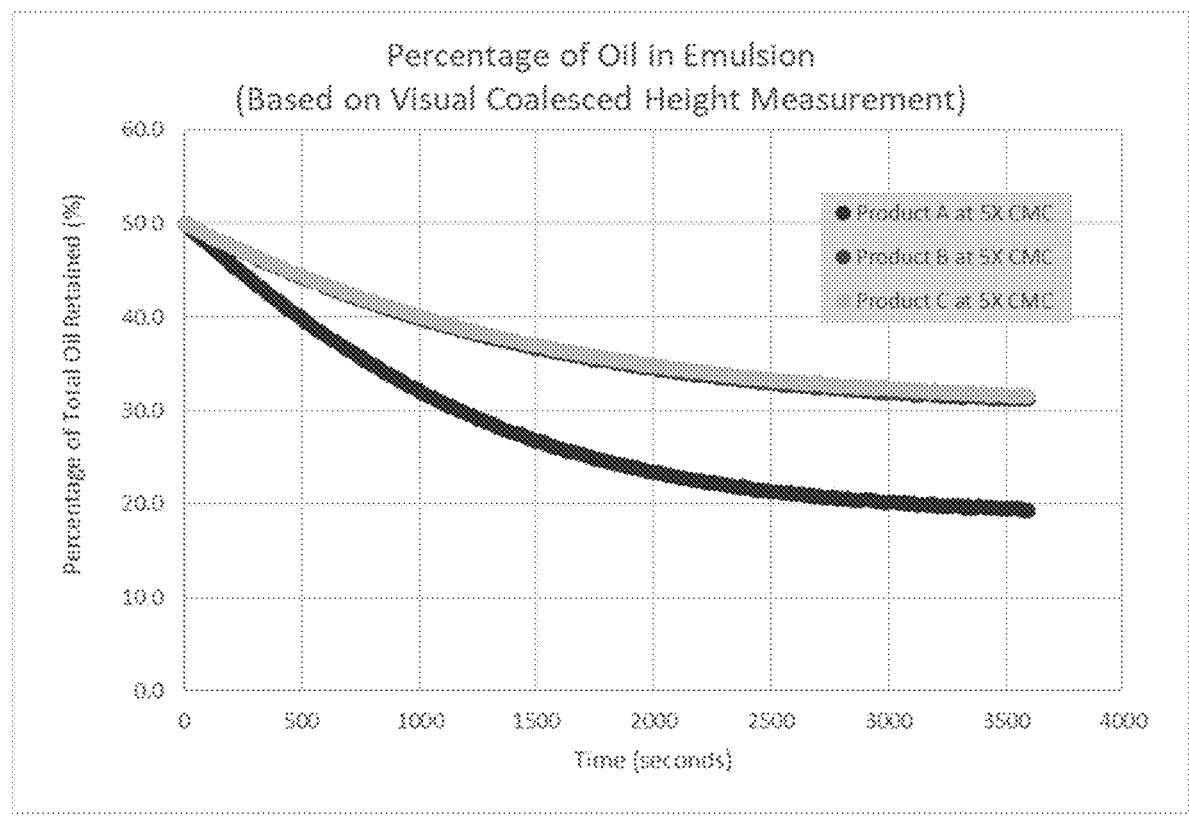
FIG. 3 is a graph showing the percentage of oil in emulsion in a column comparing three different compositions as disclosed herein.

The results of the three tests shown in FIGS. 1-3. FIGS. 1&2 are plots based on visual (camera based using the Foamscan software) observation of coalescing oil at the top of the column. Both figures show that the oil-holding capacity of Products B and C are exactly the same over a 1-hour period once they are diluted to 5×CMC. Products B and C release about 65 mm of oil (out of 120 mm total in the mixture) in the hour period, but Product A (without the synergist) gives up more than 90 mm of the oil. Therefore, the micelles in Products B and C have greater oil-holding capacity than those of Product A.

In FIG. 2, while the plot mimics that of FIG. 1, but changes the raw height of the oil data is changed into a percentage of the total retained oil in each mixture. Oil liberation tapered off for each product after about 1500 seconds, and by 1 hour (3600 seconds) plateaus were approached in each case. The plateaus were at only 24% oil retained in the case of Product A, but around 45% oil retained in the cases of Products B and C. That is a remarkable difference.

The next thing considered was the extent of homogeneity in the emulsions that are left as the oil is liberated.

FIG. 3 plots the data for the conversion of the oil height data. Here percentage of oil is calculated in the remaining lower oil/water mix (emulsion) as oil is liberated. It is important to note that this is different from the graph of FIG. 2, which was percentage of total oil retained from 0% to 100% of what was inserted into the mix. FIG. 3 refers to the percentage of oil in the emulsion. The maximum initial percentage of oil is 50%, because each emulsion was created with 82.5 mL of corn oil and 82.5 mL of aqueous phase.

As oil is liberated by coalescence, the percentage of oil in the emulsion (which can be also measured directly at each electrode probe position) decreases. In the case of Product A it drops down to 19.4% oil in the emulsion. In the case of Products B and C it drops down to around 31.5%.

While the plots of FIGS. 1-3 show the total lost oil, they do not show the distribution of oil in the emulsion by position. For instance, one may obtain an overall average 30% for two separate oil emulsions. In the first one, the percentage is only 10% oil at the bottom of the column and 50% at the top, while for the second one, it is 28% at the bottom and 32% at the top. Clearly, the second mixture is less stable and liberates more oil than the first, even though they show the same overall average of oil leakage. The electrodes of the device are used to determine the extent of oil leakage as a function of distance travelled in the column.

Figure 4:
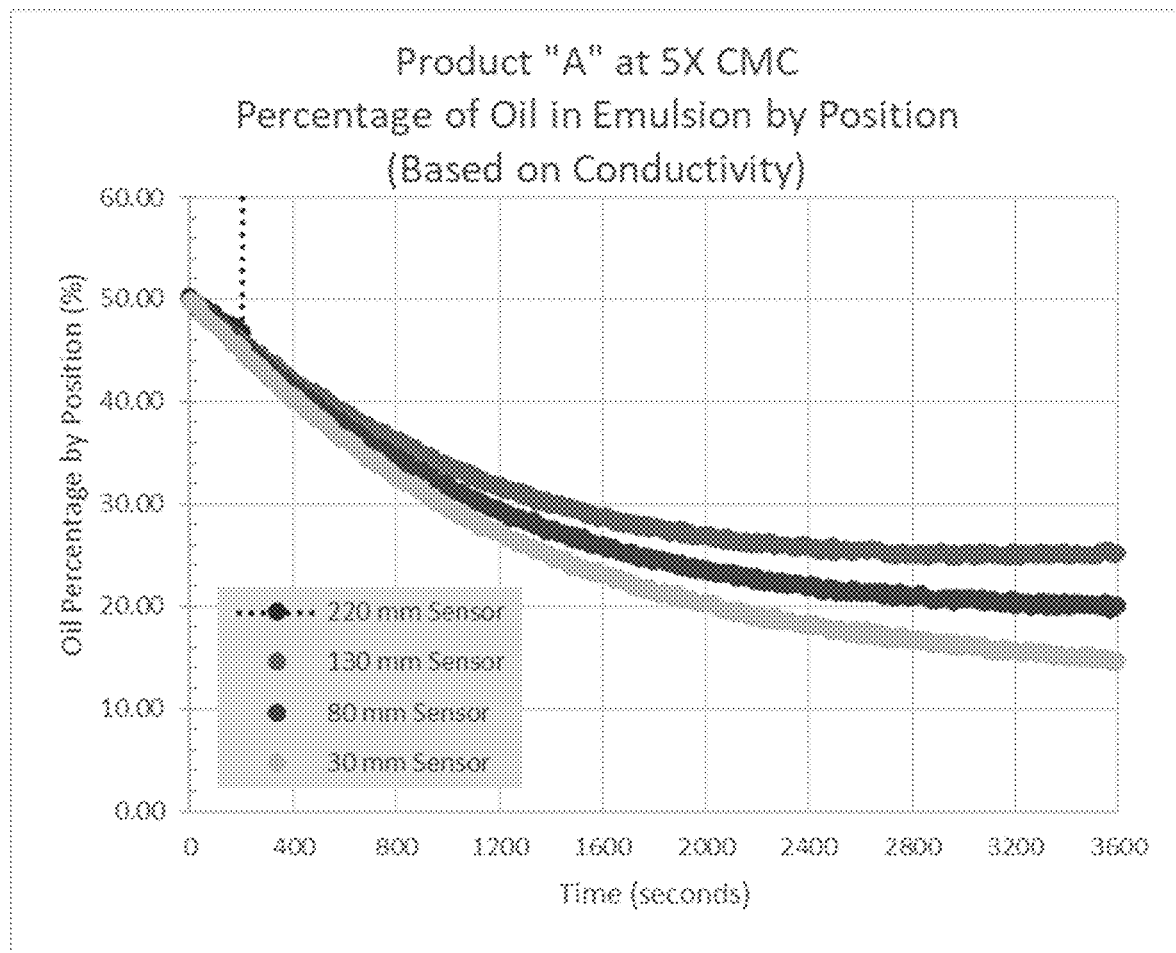
FIG. 4 is a graph showing the percentage of oil in emulsion by position in a column for Product "A".
Figure 5:
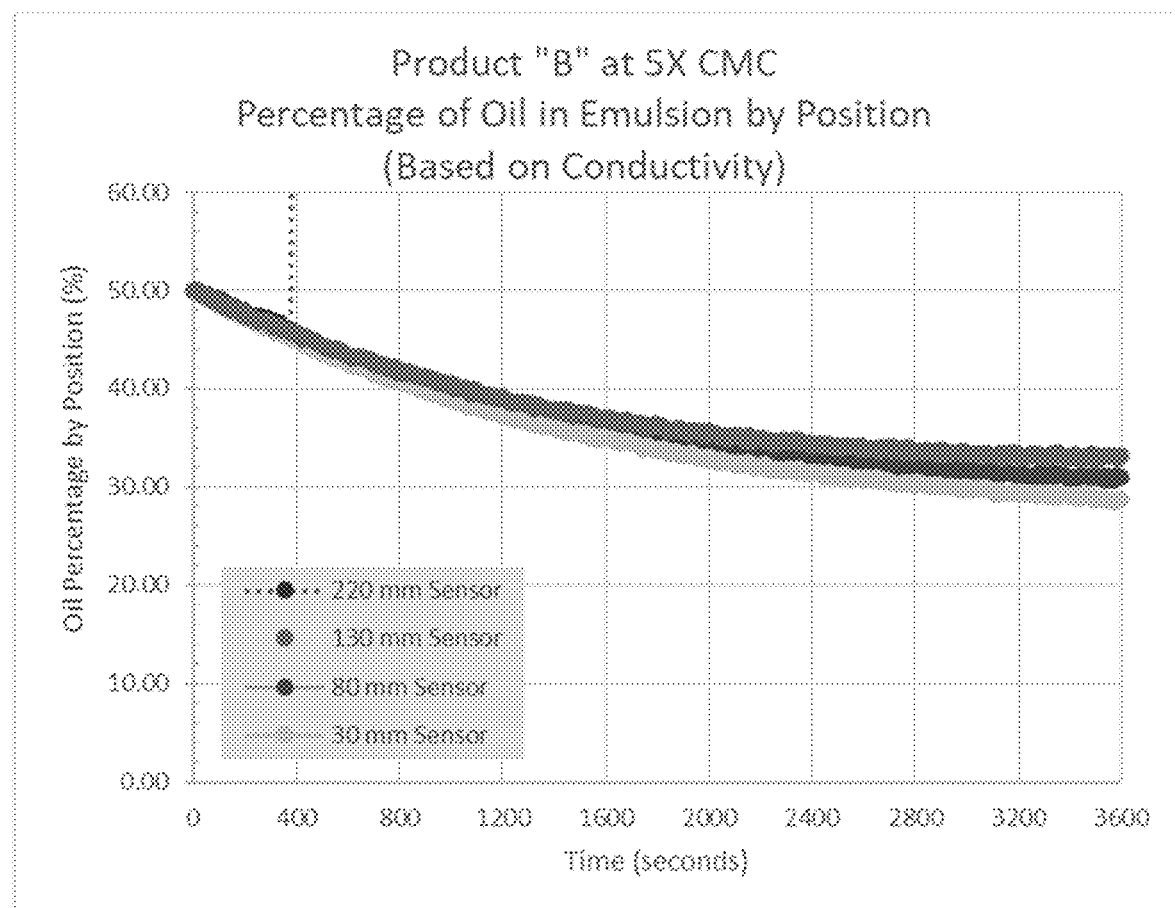
FIG. 5 is a graph showing the percentage of oil in emulsion by position in a column for Product "B".
Figure 6:
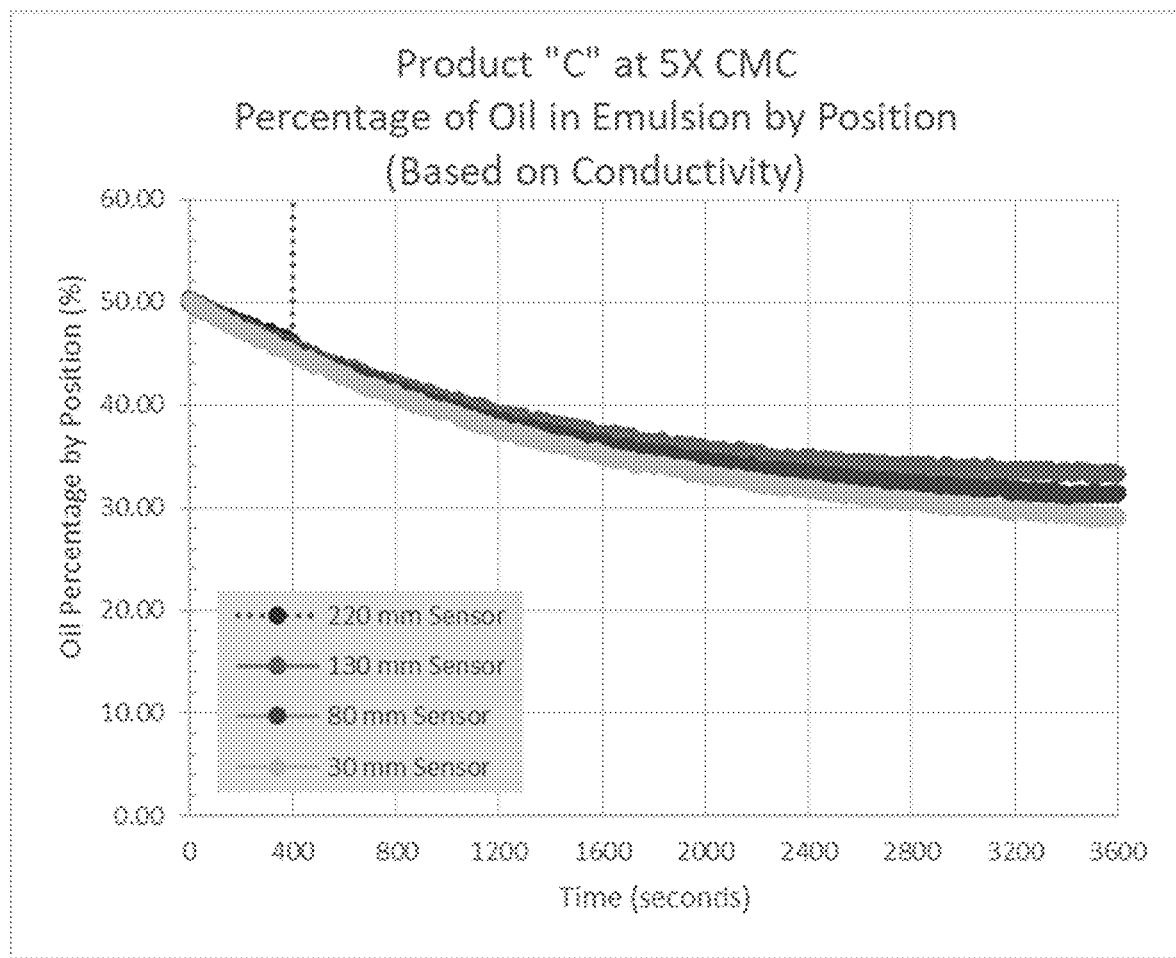
FIG. 6 is a graph showing the percentage of oil in emulsion by position in a column for Product "C".

The results are shown in the plots of FIGS. 4-6.

For the Product A at 5×CMC test (FIG. 4), the remaining emulsion after 1 hour has an overall remaining oil percentage of 19.4% (starting at 50% oil). The column distribution (percentage of oil at mm of column) is as follows: 25.2% @ 130 mm; 20.1% @ 80 mm, and 14.7% @ 30 mm. This accounts for a 10.5% difference (25.2%-14.7%) in oil density from the 130 mm mark to the 30 mm mark in the emulsion.

For Product B at 5×CMC test (FIG. 5), the remaining emulsion after 1 hour has an overall remaining oil percentage of 31.2% (starting at 50% oil). The column distribution (percentage of oil at mm of column) is as follows: 33.2% @ 130 mm; 31.0% @ 80 mm, and 28.8% @ 30 mm. This accounts for a much more modest 4.4% difference (33.2%-28.8%) in oil density from the 130 mm mark to the 30 mm mark in the emulsion.

For the Product C at 5×CMC test (FIG. 6), the remaining emulsion after 1 hour has an overall remaining oil percentage of 31.6% (starting at 50% oil). The column distribution (percentage of oil at mm of column) is as follows: 33.4% @ 130 mm; 31.4% @ 80 mm, and 29.1% @ 30 mm. Again, a much more modest 4.3% difference (33.4%-29.1%) is observed.

The results from the micelle oil holding capacity definitively show the profound effect of mixed micelle structure created by the addition of the combined SBS/sophorolipid surfactant versus the sophorolipid surfactant only when compared at the same CMC multiple.

What is claimed is:

1. A composition comprising a sophorolipid surfactant and a surfactant bio-synergist (SBS),
   wherein the sophorolipid surfactant comprising C18-unsaturated fatty acids esters with glycerol is produced by partially hydrolyzing a fermentation product of *Candida bombicola* grown with glucose; and
   wherein the SBS is a metabolite broth produced by a method comprising:
   growing yeast selected from the group consisting of *Saccharomyces cerevisiae, Kluyveromyces marxianus, Kluyveromyces lactis, Candida utilis* (Torula yeast) *Zygosaccharomyces, Pichia pastoris,* and *Hansanula polymorpha* under aerobic fermentation conditions to obtain a fermentation mixture comprising fermented yeast cells, and proteins and peptides secreted therefrom;
   subjecting the fermentation mixture to stress in order to stimulate the yeast cells to express heat shock proteins, to obtain a stressed fermentation mixture; and
   separating the stressed fermentation mixture to form a solid/precipitate and a supernatant, wherein the resultant supernatant is the SBS.

2. The composition of claim 1, wherein subjecting the fermentation mixture to stress comprises heating the fermentation mixture to 40-60° C. for at least 2 hours followed by cooling to 25° C.

3. The composition of claim 2, wherein subjecting the fermentation mixture to stress further comprises physical and/or chemical disruption of the yeast cells, or lysing of the yeast cells.

4. The composition of claim 1, wherein the separating comprises centrifuging the stressed fermentation mixture.

5. The composition of claim 1, wherein the composition comprises about 10% sophorolipid surfactant, about 20% sophorolipid surfactant, about 30% sophorolipid surfactant, about 40% sophorolipid surfactant, or about 70% sophorolipid surfactant.

6. The composition of claim 1, wherein the composition comprises about 30% SBS, about 50% SBS, about 70% SBS, about 80% SBS, or about 90% SBS.

7. The composition of claim 1, wherein a ratio of the sophorolipid surfactant to the SBS in the composition is selected from the group consisting of about 70:30, about 50:50, about 30:70, about 20:80, and about 10:90.

8. The composition of claim 1, wherein a critical micelle concentration of the composition is between about 0.1% to about 0.5% of the composition.

9. The composition of claim 1, wherein the composition retains at least about 30% oil trapped by micelles in the composition after one hour.

10. The composition of claim 1, wherein the composition retains greater than about 20% oil trapped by micelles in the composition after one hour.

* * * * *